United States Patent [19]

Ferruti et al.

[11] Patent Number: 4,929,750

[45] Date of Patent: May 29, 1990

[54] COMPOUNDS HAVING HYPOLIPEMIZING ACTIVITY

[75] Inventors: Paolo Ferruti; Giancarlo Scapini, both of Rome, Italy

[73] Assignee: Nuovo Consorzio Sanitario Nazionale, Rome, Italy

[21] Appl. No.: 224,185

[22] Filed: Jul. 22, 1988

Related U.S. Application Data

[63] Continuation of Ser. No. 929,788, Nov. 13, 1986, abandoned, which is a continuation-in-part of Ser. No. 701,858, Feb. 15, 1985, abandoned.

[30] Foreign Application Priority Data

Feb. 17, 1984 [IT] Italy ................................ 19683 A/84

[51] Int. Cl.$^5$ ............................................... C07C 69/76
[52] U.S. Cl. ...................................... 560/87; 560/195; 560/199; 514/533; 514/547
[58] Field of Search .......................... 560/195, 199, 87; 514/533, 547

[56] References Cited

FOREIGN PATENT DOCUMENTS

| 2547572 | 2/1977 | Fed. Rep. of Germany | ........ 560/87 |
| 2713506 | 10/1977 | Fed. Rep. of Germany | ........ 560/87 |
| 2715184 | 10/1977 | Fed. Rep. of Germany | ........ 560/87 |
| 1522577 | 8/1978 | United Kingdom | .................. 560/87 |

*Primary Examiner*—Paul J. Killos
*Attorney, Agent, or Firm*—Birch, Stewart, Kolasch & Birch

[57] ABSTRACT

Oligomeric and polymeric derivativies of 1,10-bis(2-hydroxyethylthio)decane, processes for the preparation thereof and their therapeutic use.

6 Claims, No Drawings

COMPOUNDS HAVING HYPOLIPEMIZING ACTIVITY

This application is a continuation, of application Ser. No. 929,788 filed on Nov. 13, 1986, which was a continuation-in-part of application Ser. No. 701,858 filed on Feb. 15, 1985, both abandoned.

The present invention concerns novel oligomeric and polymeric derivatives of 1,10-bis(2-hydroxyethylthio)-decane, known as Thiadenol, having the structure of poly(ester)s of Thiadenol and biscarboxylic acids. More specifically, the products which are the object of the invention have the following structure:

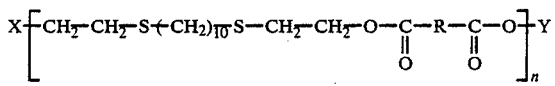

wherein the meanings of Y, n, R and X are as follows:
Y may be either —H or —CH$_2$CH$_2$S(CH$_2$)$_{10}$SCH$_2$CH$_2$OH;
n is an integer ranging between 2 and 100;
R is an organic biradical to which two carbonyl groups may be connected, such as 1,2-phenylene and 1,3-phenylene,
X may be either HO— or

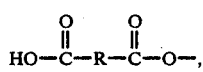

where R indicates the same organic biradical as within the parentheses.

It is apparent that only three cases must be considered, i.e.:
(1) X=HO—; Y=—H
(2) X=HO—; Y=—CH$_2$CH$_2$S(CH$_2$)$_{10}$SCH$_2$CH$_2$OH
(3) X=HO—CO—R—CO—O—; Y=—H since the case in which X=HO—CO—R—CO—O, and Y=—CH$_2$CH$_2$S(CH$_2$) S—CH$_2$—CH$_2$—OH obviously coincide with Case 1), the resulting formula being exactly the same read right-to-left instead of left-to-right.

1,10-Bis(2-hydroxyethylthio)decane, commonly marketed as Thiadenol, is one of the best drugs presently available among the hypolipemizing agents. This compound is active in several types of dislipemy, and may be advantageously used either in hypercholesterolemias or in hypertrigliceridemias and mixed hyperlipidemias. Cholesterol and triglicerides blood levels are lowered by Thiadenol. In the mean time, low-density-lipoproteins (LDLP), and very-low-density-lipoproteins (VLDLP), are substantially reduced.

The above mentioned activity of lowering plasma lipoprotein concentrations, is of benefit in preventing atherosclerosis, especially in the so-called high risk patients, i.e., those affected by hereditary hypercholesterolemia.

On the other hand, Thiadenol as such has some serious drawbacks. Its activity is not long-lasting since the drug is rapidly metabolized, and excreted. Therefore, large daily doses, and repeated administrations are required For instance, a typical treatment involves the initial administration of 0.8 g of drug every 8 hours, totalling 2.4 g a day. After an initial period, this daily dose may be reduced by one-fourth, but even so a daily intake of about 1.8 g of drug (0.6 g every 8 hours) is commonly needed, and this treatment is expected to be much prolonged over time, and possibly to be continued for life.

In several cases, such high dosages lead to undesired side-effects such as gastric pains, nausea, and vomit that compel the patients to discontinue treatment, at least temporaneously. As a rule, Thiadenol should not be employed in patients which suffer, or have suffered, from gastric or duodenal ulcers.

The above drawbacks connected with the use of Thiadenol as such, may be overcome by preparing polymeric or oligomeric derivatives of the same drug, in which the drug itself is bound to an oligomeric or polymeric structure by means of covalent bonds which can be hydrolyzed in the body fluids, thus ensuring a continuous release of drug molecules, and, consequently, constant levels of drug.

By this way, less frequent administrations and lower amounts of drug are needed to obtain the same useful pharmacological effects, and untoward side-effects due to hyperdosage can be minimized. This can be of great advantage when a chronic treatment is needed, as is usually the case.

The preparation of the above oligomeric and polymeric derivatives of Thiadenol can be carried out by heating Thiadenol with the corresponding bisacids, preferably in the presence of a suitable catalyst, and eliminating water which is continuously formed as a by-product as the esterification reaction proceeds. Instead of the free acids, reactive derivatives of the same acids can be employed, such as for instance their anhydrides, chlorides, or activated esters or amides (i.e., their N-hydroxy-succinimide esters, their N-hydroxy-benzotriazole esters, their imidazolides, their benzotriazolides, or any other known reactive derivative). The esterification reaction can be also performed starting from the free acids and Thiadenol in the presence of suitable coupling agents, such as for instance dicyclohexylcarbodiimide or other carbodiimides.

The reaction may be effected with or without solvents. The preferred procedure, however, is to use an inert solvent, such as benzene or toluene.

The molecular weight of the products, i.e., their degree of polymerization "n" (see above) could be varied at will by two means. The reagents may be reacted in equimolecular amounts, and the reaction may be either stopped before completion, to obtain lower molecular weight products, or pushed to completion, to obtain high molecular weight products. In this case, "X" and "Y" (see above), on the average, are equal to HO— and —H, respectively. Alternatively, the reagents may be reacted in a molecular ratio different from unit, and the reaction is pushed to completion. In this case, according to a well-known rule in polycondensations, the average degree of polymerization "n" depends on the molar ratio between the two monomers. It is obvious that, if the component in excess is the bis-acid, the resulting product has "X"=HO—CO—R—CO—, and "Y"-=—H; while if the excess component is Thiadenol, the product has "X"=H—, and "Y"=—CH$_2$CH$_2$—S—(CH$_2$)$_{10}$—S—CH$_2$CH$_2$OH.

As to the bis-carboxylic acids which can be used, the products will be obtained with a very large, and practically unlimited variety of acids. As a rule, however, we preferred to use bis-acids which are well known to be physiologically safe, being already present in the human body, such as for instance succinic acid, glutaric acid, adipic acid, sebacic acid, etc.

All the products tested had a very low toxicity when given orally to test animals, their $LD_{50}$ being always higher than 1,000 mg/kg, and very frequently practically impossible to be determined with accuracy.

The oligomeric and polymeric compounds of the present invention are useful for the treatment of hypertriglyceridemias, hypercholesterolemias and mixed hyperlipidemias. Low-density-lipoproteins and very low density lipoproteins are reduced and cholesterol and triglycerides blood levels are lowered. When equal doses of thiadenol and of the oligomeric and polymeric compounds of the present invention are administered to experimental animals and to humans, the drugs blood levels are longer-lasting in the case of the oligomeric and polymeric compounds of the present invention.

This involve a longer duration of action and the possibility to reduce the administration frequency, up to once a day.

For pharmaceutical use, the oligomeric and polymeric compounds of the present invention can be prepared and administered in a wide variety of oral, and parenteral dosage forms.

For preparing pharmaceutical compositions from the oligomeric and polymeric compounds described by the present invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavouring agents, solubilizers, lubricants, suspending agents, binders, or tablet disintegrating agents; it can also be an encapsulating material. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in a unit dosage form. In such a form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged form.

The quantity of active compound in a unit dose of preparation may be varied or adjusted from 50 mg to 1000 mg.

In therapeutic use the oligomeric and polymeric compounds of the present invention are administered at the initial dosage of about 0.1 mg to about 50 mg per kilogram. A dose range of about 10 mg to about 30 mg per kilogram is preferred. The dosages, however, may be varied depending upon the requirements of the patient, the severity of the condition being treated, and the compound being employed. Determination of the proper dosage for a particular situation is within the skill of the art.

In order to better elucidate the above disclosure, the following non-limitative Examples are given by way of illustration.

EXAMPLE 1

A mixture of glutaric anhydride (4.564 g, 0.04 mole), 1,10-bis(2-hydroxyethylthio)decane (14.73 g, 0.05 mole), toluene (400 ml), and 4-toluensulfonic acid (0.7 g) was refluxed 20 hours in a Soxhlet extractor filled with a suitable dehydrating agent (silica or calcium sulfate) By this way, any water formed during the reaction was continuously carried away by toluene, and removed by the dehydrating agent.

After the time indicated, the reaction mixture was extracted with 2×200 ml of water, and the water extracts discarded. The organic phase was dried ($Na_2SO_4$), and evaporated to dryness "in vacuo". The crude product was finally purified by dissolution in dichloromethane (100 ml), filtration, and precipitation by the addition of ether (700 ml). The product was thoroughly dried to constant weight "in vacuo": yield 11 g, m.p. 50–53° C. By vapour-pressure osmometry, the product had a molecular weight of 1425 dalton. Its elemental analysis gave the following results:

C 58.43%; H 8.99%. These data are in good agreement with the following structure:

$$H\left[OCH_2CH_2S(CH_2)_{10}SCH_2CH_2O\underset{O}{\overset{\|}{C}}(CH_2)_3\underset{O}{\overset{\|}{C}}O\right]_3 CH_2CH_2S(CH_2)_{10}-SCH_2CH_2OH$$

which corresponds to the general formula given above, where $n=3$, $R=(CH_2)_3$, $X=HO-$, $Y=-CH_2CH_2S(CH_2)_{10}CH_2CH_2OH$.

The calculated values for this structure are: molecular weight 1466; elemental analysis: C 58.16%; H 9.07%. The $^1H$-NMR analysis was in full agreement.

EXAMPLE 2

The same procedure as in the previous Example was followed, by substituting succinic anhydride for an equimolecular quantity of glutaric anhydride. Yield 9.6 g, m.p. 62°–64° C. The product had the following structure:

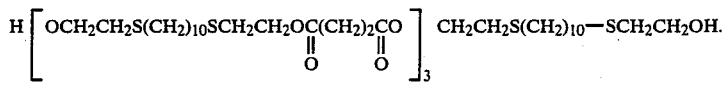

Molecular weight: calc. 1427; found 1443.
Elemental analysis:
calc. C 57.24%; H 8.90%; found C 57.36%; H 8.78%.

EXAMPLE 3

The same procedure as in the previous cases was followed, by substituting adipic acid for an equimolecular quantity of succinic or glutaric anhydride. The mixture was then refluxed for 36 hours, then the product was isolated as previously described, and finally purified by dissolution in dichloromethane, and reprecipitation with an excess of n-pentane. Yield 11.2 g. Molecular weight determination, elemental analysis, and $^1$H-NMR data were in full agreement with the following structure:

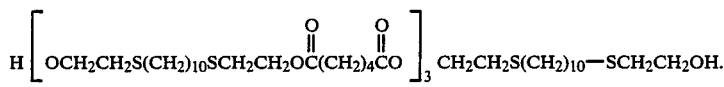

EXAMPLE 4

Following the procedure given in Example 1, glutaric anhydride (5.71 g, 0.05 mole), 1,10-bis(2-hydroxyethylthio)decane (14.73 g, 0.05 mole), toluene (400 ml), and 4-toluensulfonic acid (0.5 g) were refluxed for 30 hours. After this time, the reaction mixture was evaporated to dryness "in vacuo", and the residue was extracted with 2×100 ml of warm acetone, and dried to constant weight. Yield 11.4 g. The product had the following structure:

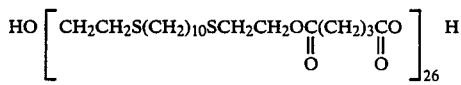

Molecular weight: calc. 10173; found 10312.
Elemental analysis: calc. C 58.32%, H 8.78%; found C 58.30%, H 9.04%.
The $^1$H-NMR analysis was in full agreement with the proposed structure.

We claim:

1. An oligomer or a polymer compound of 1,10-bis(2-hydroxyethylthio)decane and a dicarboxylic acid, of the formula

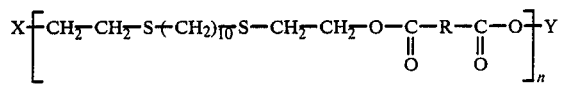

wherein
n is an integer ranging from 2 to 100
R is an organic biradical which comprises —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, 1,2-phenylene or 1,3-phenylene,
X is HO— or

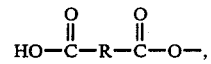

where R has the above mentioned meaning and Y is H or CH$_2$CH$_2$S(CH$_2$)$_{10}$SCH$_2$CH$_2$OH.

2. A compound according to claim 1, wherein R is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —CH$_2$CH$_2$CH$_2$CH$_2$CH$_2$CH$_2$—.

3. A compound according to claim 1, wherein R is 1,2-phenylene or 1,3-phenylene.

4. A pharmaceutical composition having hypolipemizing activity, containing as the active ingredient, at least one compound of claim 1.

5. A pharmaceutical composition having hypolipemizing activity, containing as the active ingredient, at least one compound of claim 2.

6. Pharmaceutical compositions having hypolipemizing activity, containing as the active ingredient, at least one compound of claim 3.

* * * * *